United States Patent
Hoffman

(10) Patent No.: US 11,771,953 B1
(45) Date of Patent: Oct. 3, 2023

(54) PERINEOMETER AND METHOD FOR USE OF SAME

(71) Applicant: Craig A. Hoffman, Austin, TX (US)

(72) Inventor: Craig A. Hoffman, Austin, TX (US)

(73) Assignee: Craig A. Hoffman, Austin, TX (US)

( * ) Notice: Subject to any disclaimer, the term of this patent is extended or adjusted under 35 U.S.C. 154(b) by 0 days.

(21) Appl. No.: 18/118,058

(22) Filed: Mar. 6, 2023

(51) Int. Cl.
*A63B 23/20* (2006.01)
*A61B 5/22* (2006.01)
*A61B 5/00* (2006.01)
*A61B 1/303* (2006.01)

(52) U.S. Cl.
CPC .............. *A63B 23/20* (2013.01); *A61B 1/303* (2013.01); *A61B 5/227* (2013.01); *A61B 5/7455* (2013.01)

(58) Field of Classification Search
CPC ......... A63B 23/20; A61B 1/303; A61B 5/227; A61B 5/7455; A61H 19/44; A61H 23/02; A61H 2201/1253; A61H 2201/1635; A61H 2201/1685; A61H 2201/1688; A61H 2201/169; A61H 2201/1695
See application file for complete search history.

(56) References Cited

U.S. PATENT DOCUMENTS

| | | | |
|---|---|---|---|
| 1,928,893 A * | 10/1933 | Hoard | A63B 23/20 606/198 |
| 2,507,859 A * | 5/1950 | Keller | B21C 37/292 72/370.27 |
| 2,763,265 A * | 9/1956 | Waters | A61M 29/00 482/122 |
| 3,626,931 A | 12/1971 | Bysakh | |
| 3,669,100 A | 6/1972 | Csanad | |
| 3,933,147 A | 1/1976 | Du Vall et al. | |
| 4,007,735 A | 2/1977 | Magnusson | |
| 4,048,985 A * | 9/1977 | Sasse | A63B 23/20 299/21 |
| 4,216,783 A * | 8/1980 | Kaiser | A61B 5/4337 600/561 |
| 4,396,019 A * | 8/1983 | Perry, Jr. | A61N 1/0524 600/546 |
| 4,653,514 A * | 3/1987 | Shapiro | A61B 5/227 482/121 |
| 4,911,149 A | 3/1990 | Borodulin et al. | |
| 5,184,619 A | 2/1993 | Austin | |
| 5,233,987 A | 8/1993 | Fabian et al. | |
| 5,483,832 A | 1/1996 | Pauser et al. | |
| 5,554,092 A | 9/1996 | Harpstead et al. | |
| 5,662,699 A | 9/1997 | Hamedi et al. | |
| 5,674,238 A | 10/1997 | Sample et al. | |

(Continued)

*Primary Examiner* — Garrett K Atkinson

(74) *Attorney, Agent, or Firm* — Scott Griggs; Griggs Bergen LLP

(57) ABSTRACT

A perineometer and method for use of the same are disclosed. In one embodiment of the perineometer, an elongated shaft having an external surface portion is receivable within a pelvic cavity. A sleeve is positioned lengthwise and circumferentially proximate the external surface portion. A haptic actuator having processing that separates amplitude from frequency, in response to receiving a haptic signal from a processor, generates vibrations via actuatable elements integrated into the sleeve. A sensor sensing external pressure forces at the sleeve drives a feedback signal based on the sensed external pressure forces. The haptic signal may be based on a manual signal from a manual actuator and the feedback signal.

20 Claims, 5 Drawing Sheets

(56) References Cited

U.S. PATENT DOCUMENTS

| | | | |
|---|---|---|---|
| 5,733,230 | A | 3/1998 | Sawchuck et al. |
| 5,782,745 | A | 7/1998 | Benderev |
| 5,800,501 | A | 9/1998 | Sherlock |
| 5,924,984 | A | 7/1999 | Rao |
| 6,030,338 | A | 2/2000 | Benderev |
| 6,063,045 | A | 5/2000 | Wax et al. |
| 6,169,914 | B1 | 1/2001 | Hovland et al. |
| 6,183,428 | B1 | 2/2001 | Kilgore |
| 6,217,529 | B1 | 4/2001 | Wax et al. |
| 6,625,495 | B1 | 9/2003 | Alon et al. |
| 6,672,996 | B2 | 1/2004 | Ross et al. |
| 6,741,895 | B1 * | 5/2004 | Gafni ............... A61H 19/34 600/38 |
| 6,807,444 | B2 * | 10/2004 | Tu ................. A61B 5/4381 600/549 |
| 6,905,471 | B2 * | 6/2005 | Leivseth ............ A63B 23/20 600/591 |
| 6,964,643 | B2 * | 11/2005 | Hovland ............. A61H 19/30 604/315 |
| 7,628,744 | B2 * | 12/2009 | Hoffman ............. A61B 5/227 482/148 |
| 7,645,220 | B2 * | 1/2010 | Hoffman ............ A61B 5/0538 482/148 |
| 7,955,241 | B2 * | 6/2011 | Hoffman ............ A61B 5/0538 482/148 |
| 8,936,544 | B2 * | 1/2015 | Shahoian ........... A61H 19/30 600/38 |
| 10,022,293 | B2 * | 7/2018 | Scheuring ........... A61H 19/40 |
| 10,045,906 | B2 * | 8/2018 | Shahoian ........... A61H 19/32 |
| 11,647,926 | B2 * | 5/2023 | Guay ................ A61B 5/742 600/591 |
| 2002/0055422 | A1 * | 5/2002 | Airmet .............. A63B 22/16 482/61 |
| 2003/0158475 | A1 * | 8/2003 | Johnson ............. A61B 5/055 600/410 |
| 2003/0220589 | A1 * | 11/2003 | Leivseth ............ A61B 5/227 600/591 |
| 2005/0090819 | A1 | 4/2005 | Goble |
| 2007/0010702 | A1 * | 1/2007 | Wang ................ A61L 31/10 424/422 |
| 2007/0112284 | A1 * | 5/2007 | Hoffman ............ A61B 5/053 128/905 |
| 2007/0135717 | A1 * | 6/2007 | Uenishi ............. A61B 5/6815 600/509 |
| 2009/0007672 | A1 * | 1/2009 | Pletner ............. F16F 15/00 73/579 |
| 2010/0087757 | A1 * | 4/2010 | Hoffman ............ A63B 23/20 601/46 |
| 2014/0336452 | A1 * | 11/2014 | Shahoian ........... A61H 19/40 600/38 |
| 2014/0378759 | A1 * | 12/2014 | Fang ................ A61H 19/44 600/38 |
| 2015/0245978 | A1 * | 9/2015 | Shahoian ........... A61H 19/30 601/79 |

\* cited by examiner

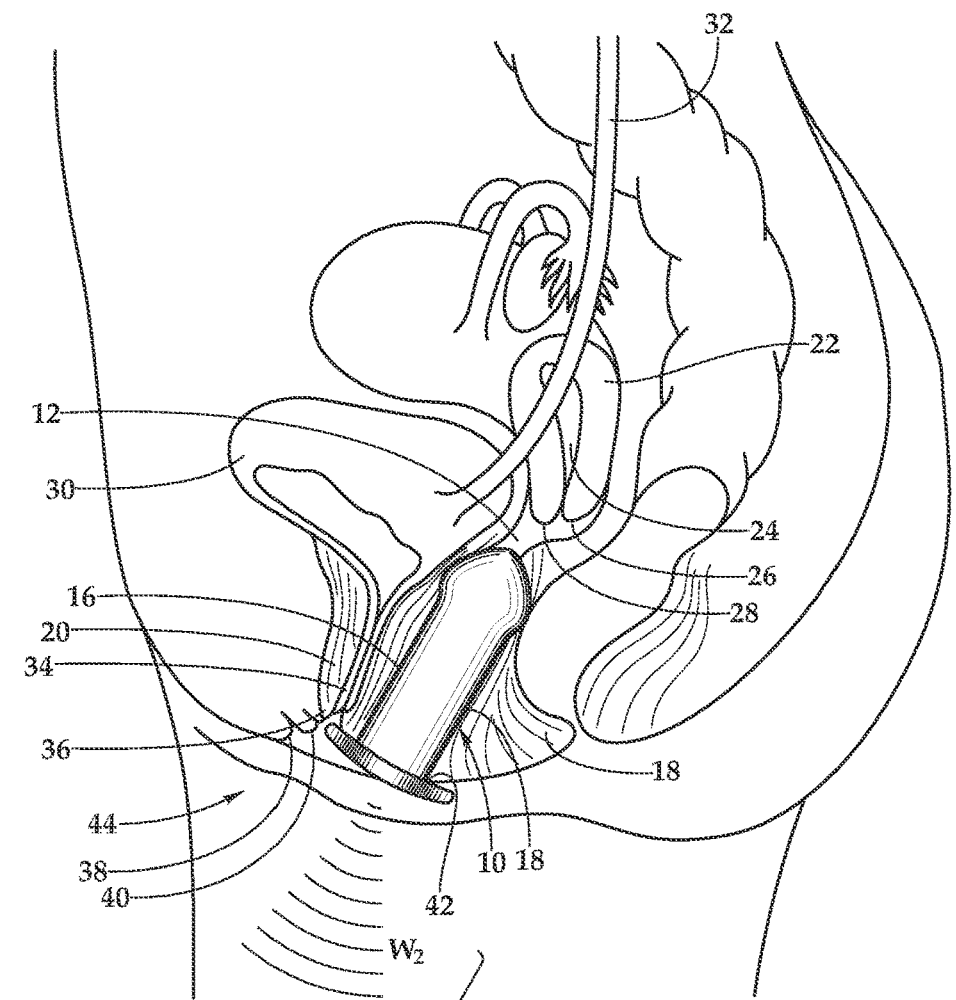
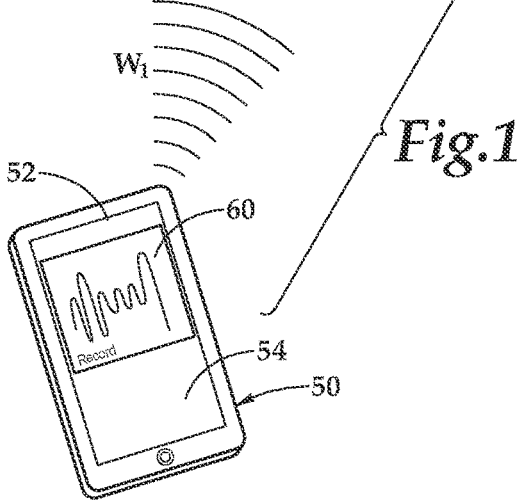
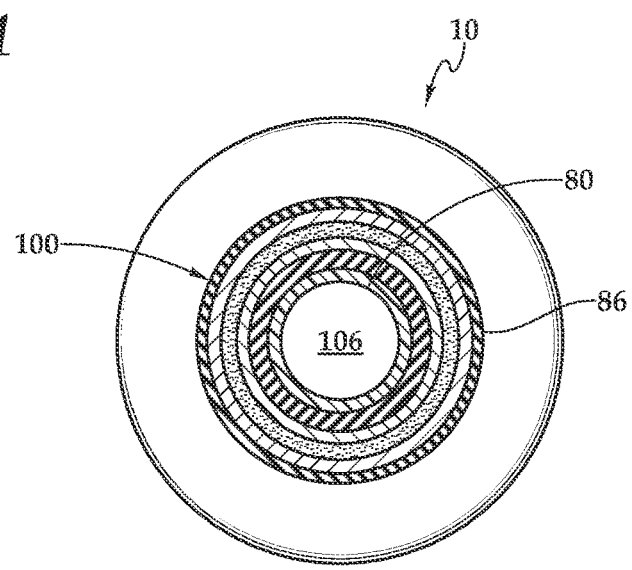
Fig.1
Fig.5

PERINEOMETER AND METHOD FOR USE OF SAME

TECHNICAL FIELD OF THE INVENTION

This invention is related to exercise devices for rehabilitating and strengthening the muscles of the pelvic floor, particularly the collective group of muscles referred to as the female pubococcygeal and related perineal musculature.

BACKGROUND OF THE INVENTION

An area of great concern to women and health care providers as well are pelvic health disorders that involve the pelvic area (bladder, pelvic floor muscle, rectum, and uterus). The lower pelvic muscles may become damaged or weakened through childbirth, lack of use, age, or as the result of surgical procedures. One of the symptoms related to a weakening of these muscles is urinary incontinence. Other pelvic disorders include chronic pelvic pain and vulvodynia (pelvic muscle dysfunction) that are sometimes experienced by young adult women. These disorders are caused by involuntary contractions (spasms) of the levator ani and perineal muscles. This condition is called vaginismus or pelvic floor tension myalgia and is accompanied by painful and difficult penetration of the vagina.

Various exercise devices have been developed in an attempt to restore the pelvic floor muscles, with the specific goal of strengthening the muscles that surround the urethra to overcome urinary incontinence in women. Notwithstanding the existence of such conventional exercise devices, there is a continuing interest in an improved exerciser that allows the patient to exercise the vaginal muscle groups in complete privacy at home or under clinical supervision, with dynamic real-time biofeedback, is simple to use, has a low risk of injury and is easy to maintain. There is a further need for a biofeedback probe and monitor for use by women who are experiencing painful pelvic spasms (pelvic floor tension myalgia), that provides visual as well as tactile feedback signals as an aid for training pelvic muscle relaxation techniques.

SUMMARY OF THE INVENTION

It would be advantageous to achieve a perineometer and method for use of the same that would significantly change the course of existing perineometers by adding features to correct existing limitations in functionality. It would also be desirable to enable a mechanical and electronics-based solution that would provide enhanced performance and improved usability with an enhanced feature set. It would be further desirable to enable a mechanical and electronics-based solution that would provide a passive exercise device for the pelvic floor muscles, including the collective group of muscles involved in sexual response, as well as intravaginal use in connection with the development, training and rehabilitation of the female pubococcygeal and related perineal musculature. To better address one or more of these concerns, a perineometer and method for use of the same are disclosed.

In one embodiment of the perineometer, an elongated shaft having an external surface portion is receivable within a pelvic cavity. A sleeve is positioned lengthwise and circumferentially proximate the external surface portion. A haptic actuator having processing that separates amplitude from frequency, in response to receiving a haptic signal from a processor, generates vibrations via actuatable elements integrated into the sleeve. A sensor sensing external pressure forces at the sleeve drives a feedback signal based on the sensed external pressure forces. The haptic signal may be based on a manual signal from a manual actuator and the feedback signal.

In another aspect, in one embodiment of the perineometer, an elongated shaft has a sleeve positioned lengthwise and circumferentially thereabout with actuatable members integrated therein. A haptic actuator has processing that separates amplitude from frequency, and, in response to receiving a haptic signal, generates vibrations, which may be a tapping sensation, via actuatable elements integrated into the sleeve. The sensor senses external pressure forces at the sleeve, to drive a feedback signal based on the sensed external pressure forces. Within the elongated shaft, memory is accessible to the processor and includes first processor-executable instructions that, when executed by a processor, cause the processor to receive the feedback signal, create the haptic signal based on the manual signal and the feedback signal, and drive the haptic signal to the haptic actuator. Second processor-accessible instructions cause the processor to access a perineometer session stored in storage, receive the feedback signal, and then create the haptic signal based on the perineometer and the feedback signal prior to driving the haptic signal to the haptic actuator. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 is a simplified sectional view of the pelvic region of the female anatomy, showing one embodiment of a perineometer inserted within the intravaginal cavity in the operative actuation position, according to the teachings presented herein;

FIG. 5 is a sectional view of the perineometer as taken along line 5-5 of FIG. 4;

DETAILED DESCRIPTION OF THE INVENTION

Figure 2:
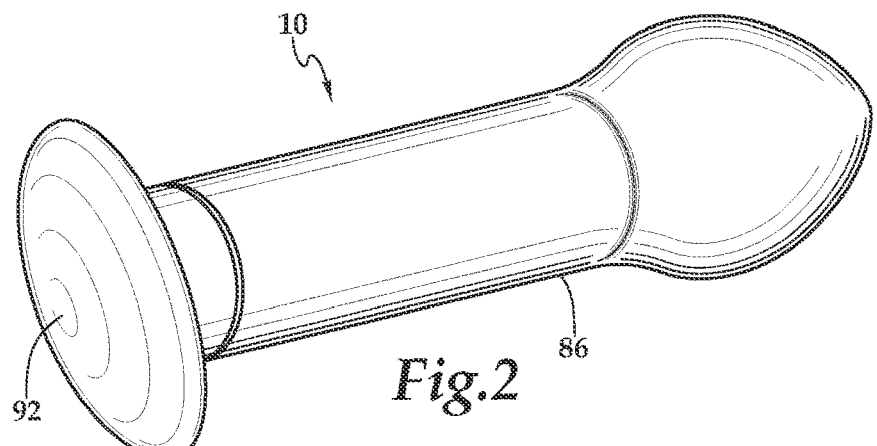
FIG. 2 is a rear perspective of view depicting the perineometer of FIG. 1A being utilized according to the teachings presented herein.
Figure 3:
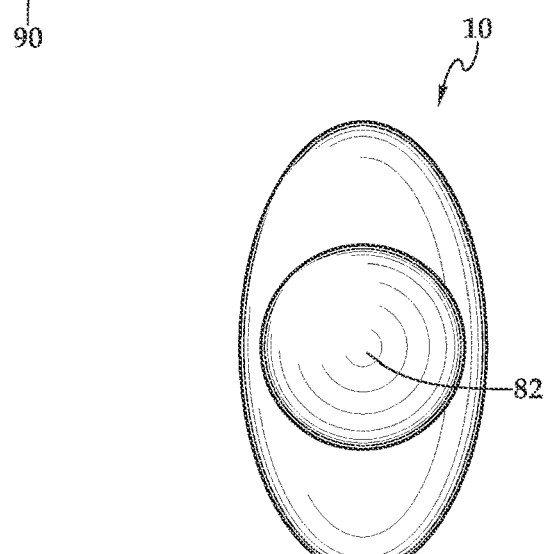
FIG. 3 is a front elevation view of the perineometer depicted in FIG. 2.
Figure 4:
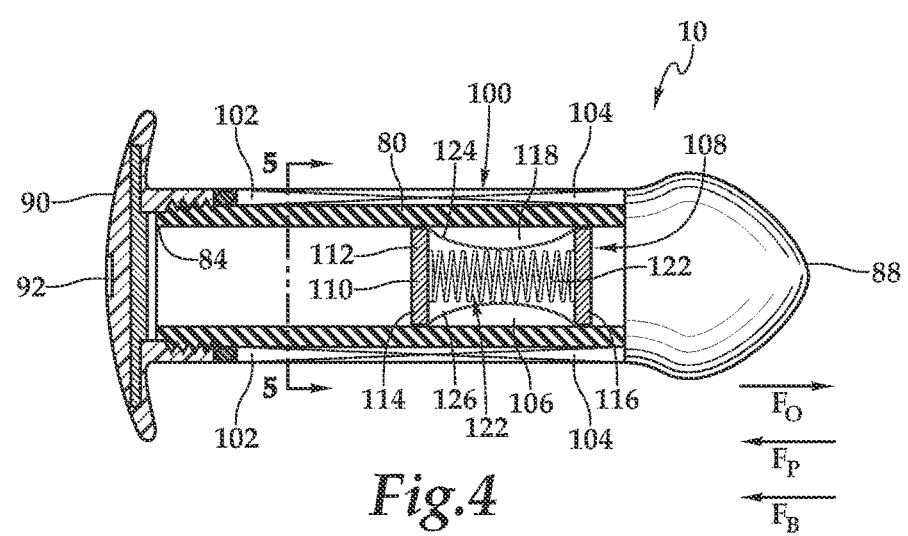
FIG. 4 is a side elevation view, partly in section, of the perineometer probe depicted in FIG. 2.
Figure 6:
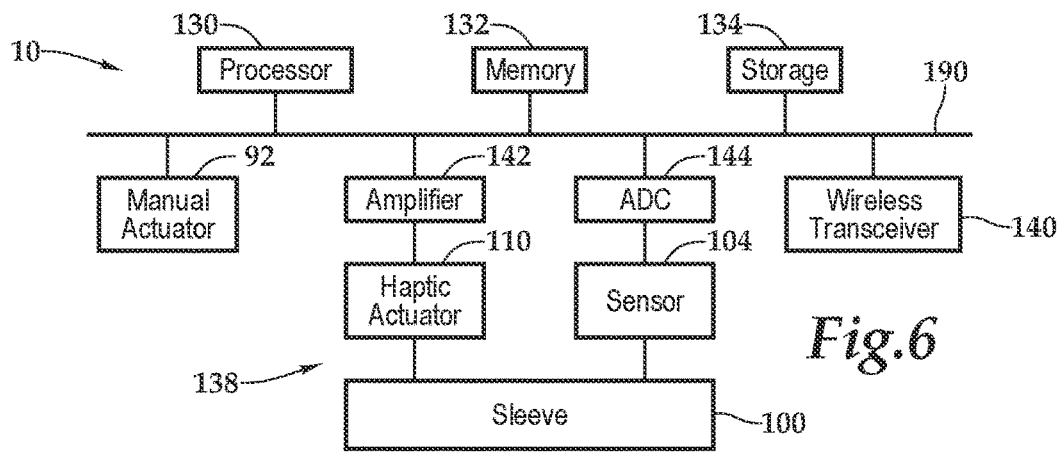
FIG. 6 is a functional block diagram of one embodiment the perineometer depicted in FIG. 1.

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Referring initially to FIG. 1, therein is depicted one embodiment of a perineometer, which is schematically illustrated and designated 10. The perineometer 10 presented herein may be inserted in the pelvic cavity 12 while the female user is reclining in the slightly elevated lithotomy position. In that position, the female user is lying on her back, knees raised, with her head slightly elevated relative to the pelvic region. Her torso is on an approximate 30-degree angle with respect to horizontal, which results in a half-sitting position, which is the preferred position for pelvic exercise training.

The lower wall 14 and the upper wall 16 of the vagina are connected to muscles, tissues, and nerves, that are indicated generally at 18, 20, and collectively referred to herein as the pubococcygeal and related perineal musculature. Also shown is the uterus 22, which has an internal void known as the uterine body cavity 24, as well as the cervix 26 and the external os 28, which is the external opening of the cervix facing the vaginal cavity 12. Other portions of the female anatomy shown in FIG. 1 include the bladder 30, ureter 32, the urethra 34, the labium minus 36, the labium majus 38, which join together in the region adjacent the clitoris 40, near the vaginal introitus 42, all of which are clustered about the region generally known as the perineum 44.

In one embodiment of the perineometer 10, the perineometer 10 includes processing that separates amplitude from frequency when generating vibrations, which may be a tapping sensation, via actuatable elements integrated into the sleeve. Further, the perineometer 10 senses external pressure forces and drives a feedback signal based on the sensed external pressure forces. As also shown, the perineometer 10 may be wirelessly communicating, as indicated by $W_1$, with a proximate smart device 50, which may be a smart phone, a smart watch, a smart wearable, a tablet, a laptop, a computer, or the like. The smart device 50 is depicted as a smart phone in FIG. 1 having a display 52 and a user interface 54, among other components, that support wireless communication with the perineometer 10, as indicated by $W_2$. As will be discussed in additional detail further below, a pairing may be created between the perineometer 10 and the proximate smart device 50. Following the pairing, in some embodiments, processing functionality may be shared between the perineometer 10 and the proximate smart device 50. Further, following the pairing, in some embodiments, the perineometer 10 and the proximate smart device 50 may share data such as recordings of the operation of the perineometer 10 or another perineometer. Such recordings may be edited or even created with the use of the smart device 50. Such a recording is illustrated as perineometer session 60.

Referring now to FIG. 2 through FIG. 6, in some embodiments, the perineometer 10 includes an elongated shaft 80 having an insertion end 82 and a base end 84 with an external surface portion 86 therebetween. The elongated shaft 80 is terminated at the insertion end 82 by a slightly enlarged and rounded head portion 88. As previously detailed in FIG. 1, the elongated shaft 80 is receivable within the pelvic cavity 12. A handle 90 is located at the base end 84. The handle 90 may also function as a closure cap. In such an embodiment, the handle 90 is fitted with threads engaging mating threads that are formed at the base end 84 of the elongated shaft 80. A manual actuator 92 is secured within the handle 90 and presented for use by a user at thereat. The manual actuator 92 may provide various manual control for regulating the applied vibration and have an ON/OFF switch integrated therewith. Additionally, in some embodiments, a display (not shown) may be positioned on the handle to provide information to a user.

In one embodiment, a sleeve 100 is positioned lengthwise and circumferentially about the elongated shaft 80 proximate the external surface portion 86. The sleeve 100 may have actuatable members 102 and a sensor 104 therein. The elongated shaft 80 surrounds a pocket portion 106. Within the pocket portion 106, electronic components 108, including a haptic actuator 110, are positioned. The haptic actuator 110 has processing that separates amplitude from frequency, and the haptic actuator 110, in response to receiving a haptic signal, generates vibrations, which may be a tapping sensation, via the actuatable elements 102 integrated into the sleeve 100. The actuatable elements 102 may include magnetic field-based actuators with a moving magnet or a moving coil, or the like, for example. The sensor 104 senses external pressure forces at the sleeve 100 in order to drive a feedback signal based on the sensed external pressure forces. The sensor 104 may include an accelerometer, gyroscope, proximity sensor, inclinometer, or the like, for example. Various components may be at least partially integrated depending on the architecture and design of the perineometer 10. By way of example, and not by way of limitation, the haptic actuator 110 and the sleeve 100 may be at least partially integrated. Similarly, the sensor 104 and the sleeve 100 may be at least partially integrated. Further, the haptic actuator 110 and the sleeve 100 may be at least partially integrated.

Returning to the haptic actuator 110, the haptic actuator 110 may be a magnetic wideband vibrational actuator, a solenoid actuator vibrator, or a linear resonant actuator vibration motor, for example. The haptic actuator 110 may include a moving mass as well as a sensing member that respond to the mass of the perineometer and to the mass of the body. By way of example, in applications using a voice coil actuator, the moving mass may include one or more permanent magnets which are set into motion by inducing a magnetic field by applying a current to voice coil proximate the one or more permanent magnets. The force of the moving mass is opposed by both the perineometer itself and the human body. Various reinforcement and dampening measures between the perineometer 10 and the moving mass therein offset the force from the perineometer 10.

In one embodiment, the haptic actuator 110 includes a magnet and a hollow member, including a coil therein, with relative longitudinal movement therebetween with thin elastic membranes interconnecting the magnet and the hollow member. In another embodiment, which is illustrated in FIG. 5, the haptic actuator 110 may include a magnet frame 112, including a magnets 114, 116 therein, and a hollow member 118, including a coil 120, which is shown as a voice coil 122, therein, that have relative longitudinal movement therebetween with thin elastic membranes 124, 126 interconnecting the magnets 114, 116 and the hollow member 118. In the embodiments with the magnet frame 112, the magnets 114, 116 within the magnet frame 112 may be within an arrangement with same polarities facing each other inside the magnet frame 112. As shown, the force $F_O$ of the moving mass, the magnets 114, 116 within the magnet frame 112, is opposed by both the perineometer $F_P$ itself and the human body $F_B$. More generally, for interactive events, such as interfacing with a portion of the human body with the human body's geometry, contours, and texture, kinaesthetic, tactile, and proprioceptic information is integrated into haptics. This vibrotactile percept requires active participation by the user, the human body, and the perineometer itself and all characteristics, from velocity to direction of movement have an influence on resulting haptic stimulus.

As mentioned, the elongated shaft 80 houses electronic components 108. More particularly, the elongated shaft 80 may house a processor 130, memory 132, and storage 134 communicatively interconnected in a busing architecture 136 within the pocket. The manual actuator 92 may also be connected to the busing architecture 136. Further, haptic elements 138 are communicatively interconnected to the busing architecture 136, as is a wireless transceiver 140. The haptic elements 138 may include the haptic actuator 110 having an amplifier 142 driving a signal thereto. As shown, the haptic actuator 110 drives a signal to the sleeve 100. As part of the haptic elements 138, the sensor 104 measures physical properties, such as sensing external pressure forces, of the sleeve 100 and drives a signal to an analog-to-digital convertor 144, which is coupled to the busing architecture 136.

As shown, the wireless transceiver 140 may be a transmitter/receiver or an antenna, for example. Communication between various smart devices, such as the smart device 50, and the perineometer 10 may be enabled by a variety of wireless methodologies employed by the wireless transceiver 140, including 802.11, 3G, 4G, Edge, WiFi, ZigBee, near field communications (NFC), Bluetooth low energy, and Bluetooth, for example. The various controls and inputs and outputs presented above are exemplary and it should be appreciated that other types of controls may be incorporated in the perineometer 10. Moreover, the electronics and form of the perineometer 10 may vary. By way of example, and not by way of limitation, an alternate embodiment of the perineometer 10 is presented in FIG. 10 hereinbelow.

The memory 132 and storage 134 are accessible to the processor 130 and include processor-executable instructions that, when executed, cause the processor 130 to execute a series of operations. In a first series of operations, the processor-executable instructions cause the processor 130 to receive the feedback signal, which is driven by the sensor 104 following the sensor 104 sensing external pressure forces. The processor is then caused to create the haptic signal based on a manual signal and the feedback signal. The manual signal is generated by the manual actuator 92 in response to manual actuation thereof. The haptic signal is then driven by the processor to the haptic actuator.

Further processor-executable instructions, when executed, cause the processor 130 to record the haptic signal as a perineometer session. The perineometer may then, by way of processor-executable instructions and the processor 130, be transmitted to the proximate smart device 50 by way of the wireless transceiver 140. Further still, the processor-executable instructions, when executed, may cause a recorded perineometer session to be accessed and with the processor-executable instructions, upon execution, then cause the processor 130 to drive the haptic signal to the haptic actuator 110.

The recorded perineometer session may originate from the perineometer 10 or other perineometer, other male or female, stimulation aid, or other computing device. In some implementations, to this end, the processor-executable instructions may cause the processor 130 to download a perineometer session via a combination of the wireless transceiver 140 and the proximate smart device 50 such that a haptic signal associated with the downloaded perineometer session is caused by the processor 130 to be driven to the haptic actuator 110.

The memory 132 may further include processor-executable instructions that, when executed by the processor 130, cause the processor 130 to execute a manual tapping output mode. In one operational mode, the vibration frequency range of the haptic actuator 110 may be between 0 Hz to 80 Hz. In another operational mode, the vibration frequency range of the haptic actuator 110 may be between 0 Hz to 65 Hz.

Figure 7:
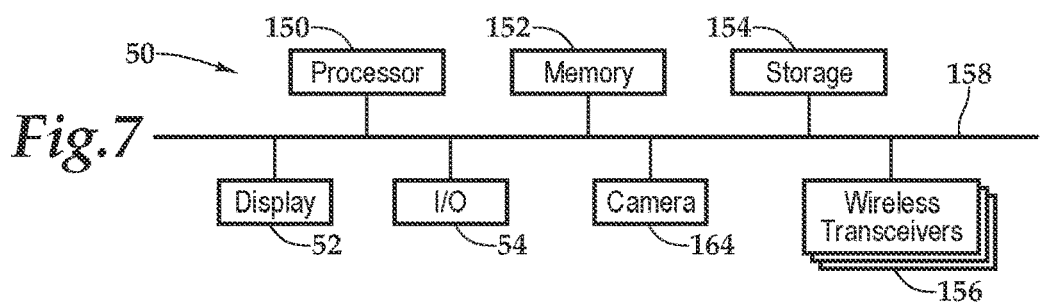
FIG. 7 is a functional block diagram of one embodiment of a smart device depicted in FIG. 1.

Referring now to FIG. 7, the proximate smart device 50 may be a wireless communication device of the type including various fixed, mobile, and/or portable devices. To expand rather than limit the discussion of the smart device 50, such devices may include, but are not limited to, cellular or mobile smart phones, tablet computers, smartwatches, computers, and so forth. The smart device 50 may include a processor 150, memory 152, storage 154, and multiple transceivers 156 interconnected by a busing architecture 158 that also supports the display 52, the I/O panel 54, and a camera 164. It should be appreciated that although a particular architecture is explained, other designs and layouts are within the teachings presented herein.

In operation, the teachings presented herein permit the smart device 50 such as a smartphone to form a pairing with the perineometer 10 and operationally influence the perineometer 10, when the smart device 50 is proximate to the perineometer 50. As shown, the proximate smart device 50 includes the memory 152 accessible to the processor 150 and the memory 152 includes processor-executable instructions that, when executed, cause the processor 150 to provide an interface for an operator that includes an interactive application for viewing the status of the perineometer 10. The processor 150 is caused to present a menu for controlling the perineometer 10. The processor 150 is then caused to receive an interactive instruction from the user and forward a control signal via the wireless transceiver 140, for example, to implement the instruction at the perineometer 10. The processor 400 may also be caused to generate various reports about the operation of the perineometer 10.

The memory 152 and storage 154 are accessible to the processor 150 and include processor-executable instructions that, when executed, cause the processor 150 to execute a series of operations. In a first series of operations, the processor-executable instructions cause the processor 150 to send and receive data with respect to the perineometer 10. The data may include operational data or a perineometer session, for example. In a second series of operations, the processor-executable instructions cause the processor 150 to send and receive perineometer sessions with another device. In a third series of operations, the processor-executable instructions cause the processor 150 to edit, including create, a perineometer session.

Figure 8:
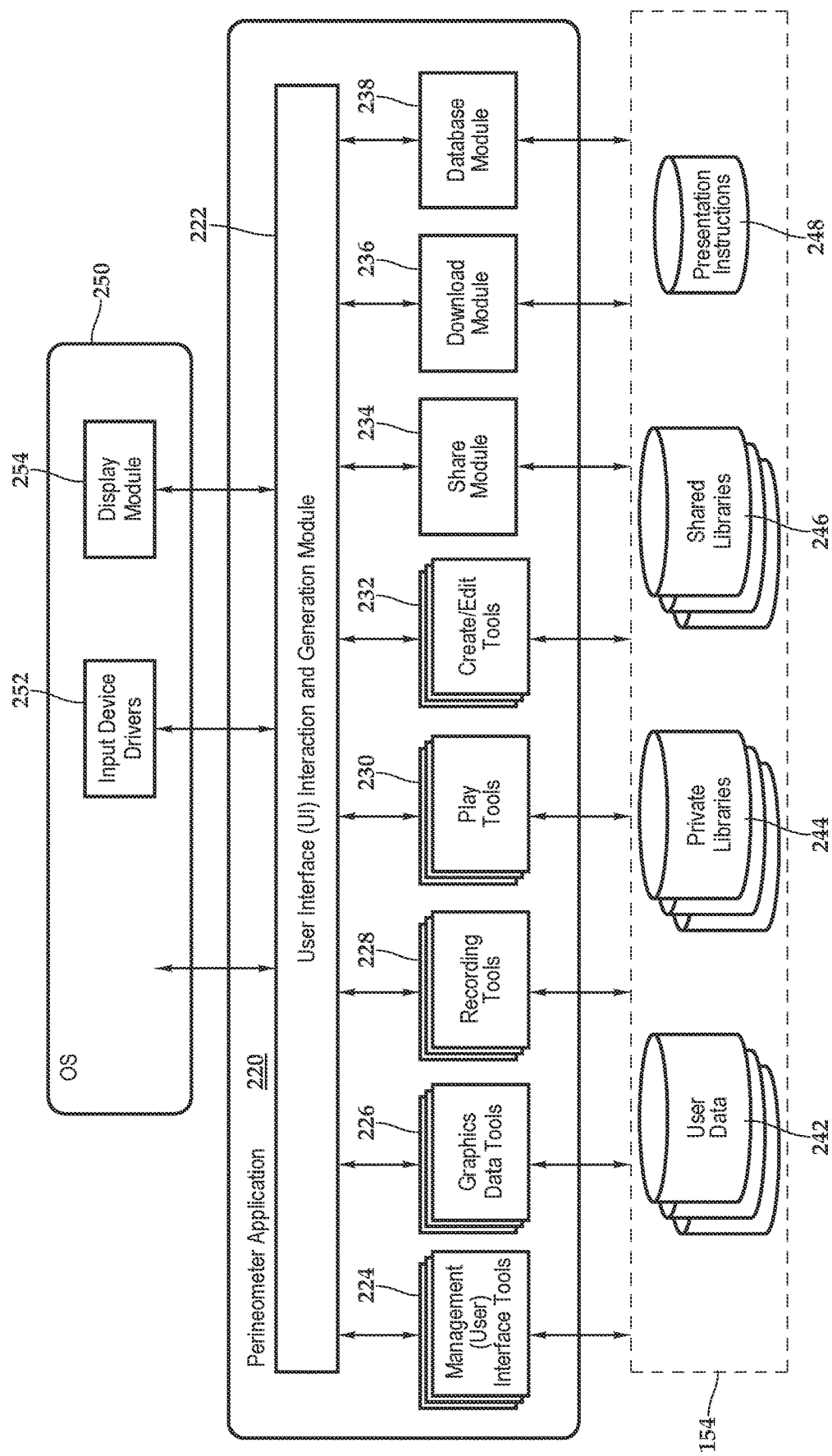
FIG. 8 is a conceptual module diagram depicting a software architecture of a perineometer application of some embodiments.

FIG. 8 conceptually illustrates the software architecture of a perineometer application 220 of some embodiments that may render data, such as operational data about the perineometer or a perineometer session. In some embodiments, the perineometer application 220 is a stand-alone application or is integrated into another application, while in other embodiments the application might be implemented within an operating system 230. Furthermore, in some embodiments, the perineometer application 220 is provided as part of a server-based solution or a cloud-based solution. In some such embodiments, the application is provided via a thin client. That is, the application runs on a server while a user interacts with the application via a separate machine or device remote from the server. In other such embodiments, the application is provided via a thick client. That is, the application is distributed from the server to the client machine and runs on the client machine.

The perineometer application 220 includes a user interface (UI) interaction and generation module 222, management (user) interface tools 224, graphics data tools 226, recording tools 228, play tools 230, creating/editing tools 232, a share module 234, a download module 236, and a database module 238. The perineometer application 220 has access to the user data database 242, private libraries database 242, shared libraries database 246, and presentation instructions 248, which presents instructions for the operation of the perineometer application 220. In some embodiments, storages 240, 242, 244, 246, 248 are all stored in one physical storage. In other embodiments, the storages 240, 242, 244, 246, 248 are in separate physical storages, or one of the storages is in one physical storage while the other is in a different physical storage.

The perineometer application 220, in one implementation, provides a database of all pertinent information required for interacting with a perineometer and support for perineometer sessions, including saving, publishing—publicly and privately, creating, and editing. The graphics data tools 226 creates a visual representation of a perineometer session for review and edit. The recording tools 228, play tools 230, and create/edit tools 232 provide the user with the set of programming tools to interact with the perineometer session under design. The share module 234 then provides the application support for sharing the perineometer session and the download module 236 supports downloading various perineometer sessions from other devices. The database module 238 may be executed to obtain data from any of the available databases, including the user data database 242, the private libraries database 242, and the shared libraries database 246, for example.

In the illustrated embodiment, FIG. 8 also includes an operating system 250 that includes input device driver(s) 252 and a display module 254. In some embodiments, as illustrated, input device drivers 252 and a display module 254 are part of the operating system 250 even when the perineometer application 220 is an application separate from the operating system 250. The input device drivers 252 may include drivers for translating signals from a keyboard, mouse, touchpad, tablet, touch screen, gyroscope, or accelerometer, for example. A user may use one or more of these input device drivers 252, which send signals to their corresponding device driver, in combination with the display module 254 to interact with perineometer application 220. The device driver then translates the signals into user input data that is provided to the UI interaction and generation module 222.

Figure 9:
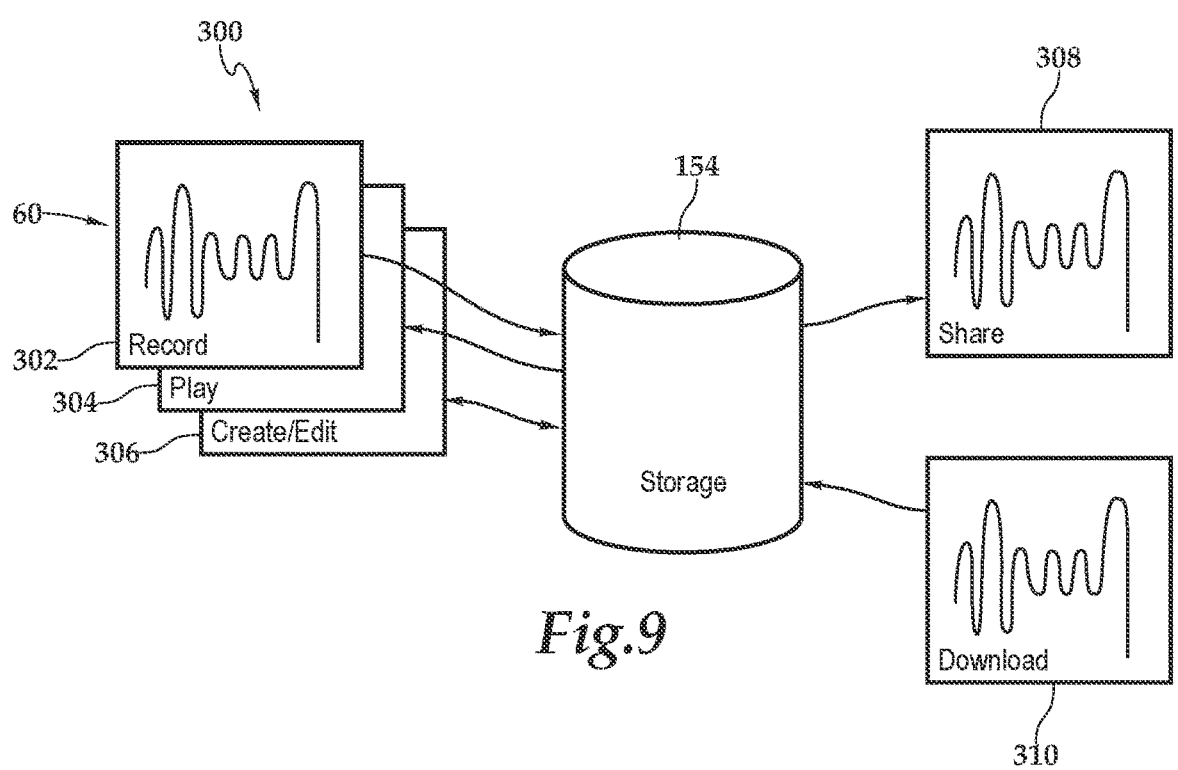
FIG. 9 is a functional block diagram depicting various operational modes of the perineometer shown herein.

In one operational embodiment, referring to FIG. 9, a graphical representation 300 of many functionalities, including recording, playing, creating/editing, sharing, and downloading of various perineometer sessions 302, 304, 306, 308, 310 is depicted. As shown, the storage 154 of the smart device 50 may utilized with the perineometer application 220, as a programmable interface, to record the perineometer session 302, play the perineometer session 304, or create/edit the perineometer session 306 as well share perineometer session 308 or download the perineometer session 310.

Figure 10:
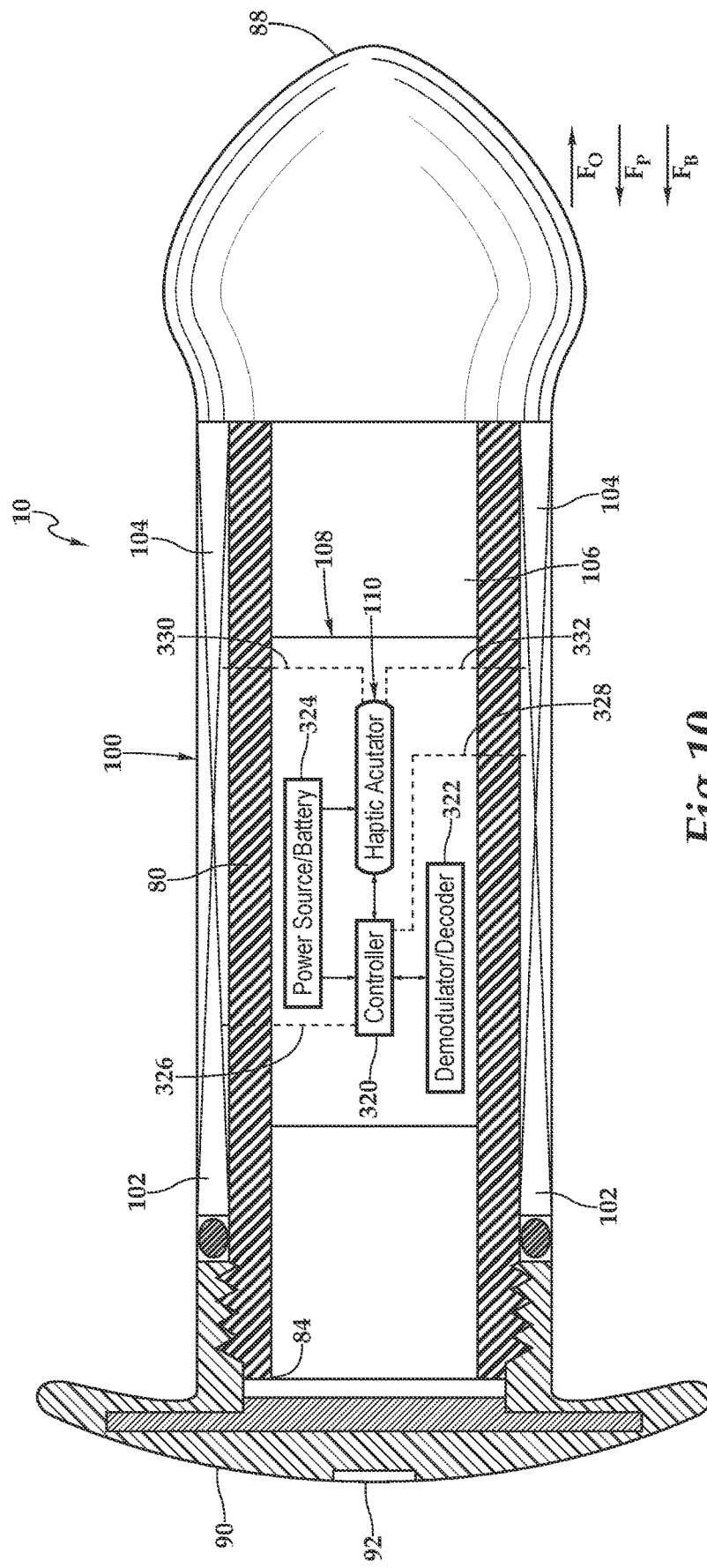
FIG. 10 is a conceptualized functional block diagram of another embodiment of the perineometer probe according to the teachings presented herein.

Referring now to FIG. 10, a further embodiment of the perineometer 10 is depicted. Within the pocket portion 106, electronic components 108, including the haptic actuator 110, are positioned. More particularly, the electronic components include a controller 320 having driver functionality that is communicatively disposed with the haptic actuator 110. With respect to driver functionality, the controller 320 may be a haptic driver that may operate a concentric rotating motor, or linear resonant actuator (LRA), or eccentric rotating mass (ERM) vibration motor, for example. The controller 320 in conjunction the haptic actuator 110 may reduce the amperage requirements of the perineometer 10 to reduce battery life. A demodulator/decoder is positioned in communication with the controller 320. A power source/battery 324 provides power to the electronic components. As shown, communication lines 326, 328 connect the controller to the actuatable members 102 and the sensor 104. Additionally, communication lines 330, 332 connect the haptic actuator 110 to the actuatable members 102 and the sensor 104. It should be appreciated that although a particular positioning of communication lines 326, 328, 330, 332 is depicted, the number and positioning of the communication lines 326, 328, 330, 332 may vary with the architectural requirements of the perineometer 10, or a component thereof, such as the haptic actuator 110.

In one embodiment, the controller 320 receives various signals from the sensors 104. The controller 320 may then access the demodulator/decoder 322. The demodulator/decoder 322 may include a waveform memory, in a look-up format, for example, that stores one or more preprogrammed waveforms corresponding to a portion of the various signals received from the sensors. The controller 320 may then provide a haptic signal to the haptic actuator 110, which may produce different vibrations, which may be taping sensations, in response to receiving different haptic signals.

In this manner, the perineometer 10 provides a passive exercise device for the pelvic floor muscles, including the collective group of muscles involved in sexual response, as well as intravaginal use in connection with the development, training and rehabilitation of the female pubococcygeal and related perineal musculature. Moreover, the perineometer 10 provides real-world muscle contraction feedback that is continuously adjustable by the user.

The order of execution or performance of the methods and data flows illustrated and described herein is not essential, unless otherwise specified. That is, elements of the methods and data flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:
1. A perineometer comprising:
an elongated shaft having an insertion end and a base end with an external surface portion therebetween, the elongated shaft receivable within a pelvic cavity, the elongated shaft housing a processor, memory, and storage communicatively interconnected in a busing architecture;
a manual actuator communicatively interconnected to the busing architecture, the manual actuator generating a manual signal in response to manual actuation thereof;

a sleeve positioned lengthwise and circumferentially about the elongated shaft, the sleeve having actuatable members integrated therein;

a haptic actuator communicatively interconnected to the busing architecture, the haptic actuator having processing that separates amplitude from frequency, the haptic actuator, in response to receiving a haptic signal, generating a plurality of vibrations via the actuatable members integrated into the sleeve;

a sensor configured for sensing external pressure forces at the sleeve, the sensor being communicatively interconnected to the busing architecture, the sensor driving a feedback signal based on the sensed external pressure forces; and the memory being accessible to the processor, the memory including processor-executable instructions that, when executed by a processor, cause the processor to:

receive the feedback signal, create the haptic signal based on the manual signal and the feedback signal, and drive the haptic signal to the haptic actuator.

2. The perineometer as recited in claim 1, further comprising a wireless transceiver communicatively interconnected to the busing architecture, the wireless transceiver configured to pair with a proximate smart device.

3. The perineometer as recited in claim 2, wherein the memory further comprises second processor-executable instructions that, when executed by the processor, cause the processor to:

record the haptic signal as a perineometer session.

4. The perineometer as recited in claim 2, wherein the memory further comprises second processor-executable instructions that, when executed by the processor, cause the processor to:

record the haptic signal as a perineometer session, and transmit the perineometer session via the wireless transceiver to the proximate smart device.

5. The perineometer as recited in claim 2, wherein the memory further comprises second processor-executable instructions that, when executed by the processor, cause the processor to:

record the haptic signal as a perineometer session, access the perineometer session, and drive the haptic signal to the haptic actuator.

6. The perineometer as recited in claim 2, wherein the memory further comprises second processor-executable instructions that, when executed by the processor, cause the processor to:

download a perineometer session via a combination of the wireless transceiver and the proximate smart device, the perineometer session including a second haptic signal.

7. The perineometer as recited in claim 2, wherein the memory further comprises second processor-executable instructions that, when executed by the processor, cause the processor to:

download a perineometer session via a combination of the wireless transceiver and the proximate smart device, the perineometer session including a second haptic signal, and drive the second haptic signal to the haptic actuator.

8. The perineometer as recited in claim 1, wherein the haptic actuator further comprises a vibration frequency range of 0 Hz to 80 Hz.

9. The perineometer as recited in claim 1, wherein the haptic actuator further comprises a manual tapping output mode.

10. The perineometer as recited in claim 1, wherein the haptic actuator further comprises a magnetic wideband vibrational actuator.

11. The perineometer as recited in claim 1, wherein the haptic actuator further comprises a magnet and a hollow member, including a voice coil therein, have relative longitudinal movement therebetween with thin elastic membranes interconnecting the magnet and the hollow member.

12. The perineometer as recited in claim 1, wherein the haptic actuator further comprises an actuator selected from the group consisting of a magnetic wideband vibrational actuator, a solenoid actuator vibrator, and a linear resonant actuator vibration motor.

13. The perineometer as recited in claim 1, wherein the haptic actuator comprises access to a waveform memory.

14. The perineometer as recited in claim 1, wherein the haptic signal further comprises an amplifier-modulated haptic signal.

15. The perineometer as recited in claim 1, further comprising an amplifier interposed between the haptic actuator and the busing architecture.

16. The perineometer as recited in claim 1, wherein the haptic actuator and the sleeve are at least partially integrated.

17. The perineometer as recited in claim 1, wherein the sensor and the sleeve are at least partially integrated.

18. The perineometer as recited in claim 1, wherein the haptic actuator and the sensor are at least partially integrated.

19. A perineometer comprising:

an elongated shaft having an insertion end and a base end with an external surface portion therebetween, the elongated shaft receivable within a pelvic cavity, the elongated shaft housing a processor, memory, and storage communicatively interconnected in a busing architecture;

a sleeve positioned lengthwise and circumferentially about the elongated shaft, the sleeve having actuatable members integrated therein;

a haptic actuator communicatively interconnected to the busing architecture, the haptic actuator having processing that separates amplitude from frequency, the haptic actuator, in response to receiving a haptic signal, generating a plurality of vibrations via the actuatable members integrated into the sleeve;

a sensor configured for sensing external pressure forces at the sleeve, the sensor being communicatively interconnected to the busing architecture, the sensor driving a feedback signal based on the sensed external pressure forces; and the memory being accessible to the processor, the memory including processor-executable instructions that, when executed by a processor, cause the processor to:

access a perineometer session stored in storage, and receive the feedback signal, create the haptic signal based on the perineometer session and the feedback signal, and drive the haptic signal to the haptic actuator.

20. A perineometer comprising:

an elongated shaft having an insertion end and a base end with an external surface portion therebetween, the elongated shaft receivable within a pelvic cavity, the elongated shaft housing a processor, memory, storage, and a wireless transceiver communicatively interconnected in a busing architecture;

a manual actuator communicatively interconnected to the busing architecture, the manual actuator generating a manual signal in response to manual actuation thereof;

a sleeve positioned lengthwise and circumferentially about the elongated shaft, the sleeve having actuatable members integrated therein;

a haptic actuator communicatively interconnected to the busing architecture, the haptic actuator having processing that separates amplitude from frequency, the haptic actuator, in response to receiving a haptic signal, generating a plurality of vibrations via the actuatable members integrated into the sleeve;

the haptic actuator including a magnet and a hollow member, including a coil therein, and having relative longitudinal movement therebetween with thin elastic membranes interconnecting the magnet and the hollow member;

a sensor configured for sensing external pressure forces at the sleeve, the sensor being communicatively interconnected to the busing architecture, the sensor driving a feedback signal based on the sensed external pressure forces; and the memory being accessible to the processor, the memory including first processor-executable instructions that, when executed by a processor, cause the processor to:

receive the feedback signal, create the haptic signal based on the manual signal and the feedback signal, and drive the haptic signal to the haptic actuator.

* * * * *